United States Patent
Gwon et al.

(10) Patent No.: US 6,176,878 B1
(45) Date of Patent: Jan. 23, 2001

(54) ACCOMMODATING INTRAOCULAR LENS

(75) Inventors: Arlene Gwon, Newport Beach; Daniel G. Brady, San Juan Capistrano, both of CA (US)

(73) Assignee: Allergan Sales, Inc., Irvine, CA (US)

( * ) Notice: Under 35 U.S.C. 154(b), the term of this patent shall be extended for 0 days.

(21) Appl. No.: 09/213,976

(22) Filed: Dec. 17, 1998

(51) Int. Cl.$^7$ ........................................ A61F 2/16
(52) U.S. Cl. .................. 623/6.37; 623/6.38; 623/6.39
(58) Field of Search ........................... 623/6.37, 6.39, 623/6.38

(56) References Cited

U.S. PATENT DOCUMENTS

| | | |
|---|---|---|
| 4,253,199 | 3/1981 | Banko . |
| 4,254,509 | 3/1981 | Tennant . |
| 4,409,691 | 10/1983 | Levy . |
| 4,790,847 | 12/1988 | Woods . |
| 4,842,601 | 6/1989 | Smith . |
| 4,888,012 | 12/1989 | Horn et al. . |
| 4,888,015 | 12/1989 | Domino . |
| 4,932,968 | 6/1990 | Caldwell et al. . |
| 4,976,732 | 12/1990 | Vorosmarthy . |
| 4,994,082 | 2/1991 | Richards et al. . |
| 5,019,098 | 5/1991 | Mercier . |
| 5,171,266 | 12/1992 | Wiley et al. . |
| 5,173,723 | 12/1992 | Volk . |
| 5,275,623 | 1/1994 | Sarfarazi . |
| 5,443,506 | 8/1995 | Garabet . |
| 5,476,514 | 12/1995 | Cumming . |
| 5,496,366 | 3/1996 | Cumming . |
| 5,562,731 | 10/1996 | Cumming . |
| 5,578,081 | 11/1996 | McDonald . |
| 5,607,472 | 3/1997 | Thompson . |
| 5,674,282 | 10/1997 | Cumming . |

FOREIGN PATENT DOCUMENTS

| | | |
|---|---|---|
| 337390 | 10/1989 | (EP) . |
| 9615734 | 5/1996 | (WO) . |
| 9625126 | 8/1996 | (WO) . |
| 9743984 | 11/1997 | (WO) . |

OTHER PUBLICATIONS

Thornton, Accommodation in Pseudophakia, 25, pp. 159–162.

Primary Examiner—Michael J. Milano
(74) Attorney, Agent, or Firm—Stout, Uxa, Buyan & Mullins; Frank J. Uxa

(57) ABSTRACT

Intraocular lenses include an optic adapted to focus light toward a retina of an eye and a movement assembly coupled to the optic. The optic includes a far vision correction power for infinity reduced by a diopter power increment. The movement assembly is adapted to cooperate with the eye to move the optic bidirectionally, that is anteriorly in the eye and posteriorly in the eye, for example, from a neutral resting position in the eye, to effect positive accommodating movement of the optic and negative accommodating movement of the optic, respectively. Methods of inserting such intraocular lenses into an eye are also provided.

25 Claims, 3 Drawing Sheets

ACCOMMODATING INTRAOCULAR LENS

BACKGROUND OF THE INVENTION

The present invention is directed to intraocular lenses (IOLs). More particularly, the invention relates to IOLs which are adapted to provide bidirectional accommodating movement in the eye.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focussing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. These lenses are biased to be located in the posterior-most position in the eye under rest or resting conditions. When near focus is desired, the ciliary muscle contracts and the lens moves forwardly (positive accommodation). In the absence of ciliary muscle contraction, the lens moves rearwardly to its posterior-most resting position. One problem that exists with such IOLs is that they often cannot move sufficiently to obtain the desired accommodation.

It would be advantageous to provide IOLs adapted for accommodating movement which can achieve an increased amount of accommodation.

SUMMARY OF THE INVENTION

New accommodating IOLs have been discovered. The present accommodating IOLs take advantage of the ability of the eye to move the present IOLs bidirectionally, that is both forwardly (anteriorly) and rearwardly (posteriorly), in the eye in response to normal accommodative stimuli. Thus, the present lenses provide for controlled vision correction or focusing for both near objects and far or distant objects. Further, because bidirectional accommodating movement is provided and the optics of the IOLs have optical powers which take into account such bidirectional movement, a greater overall range of accommodation is often achieved. Thus, the present IOLs provide for controlled accommodating movement and/or an increased range of accommodating movement. The present IOLs are straightforward in construction, can be implanted or inserted into the eye using systems and procedures which are well known in the art and function effectively with little or no additional treatments or medications being required.

In one broad aspect of the present invention, intraocular lenses (IOLs) are provided and comprise an optic and a movement means or movement assembly. The optic is adapted to focus light toward the retina of an eye and has a far vision correction power for infinity reduced by a diopter power increment. For example, the optic has an optical power or a vision correction power which results in myopia at a neutral resting state of the eye. That is, the wearer of such an IOL experiences relative myopia viewing a distant (far) object, for example, an object located 20 or more meters from the eye, with the optic in a neutral resting state (or position) of the eye.

As used herein, the term "neutral resting state" refers to the state of the eye which exists without visual stimuli, for example, in a totally darkened room or in a luminous but completely empty visual field. Such a "neutral resting state" can be considered the natural resting state of the eye. The neutral resting state of the eye can be referred to as "tonic accommodation", "space myopia" and "sky myopia". Viewed from a different perspective, the neutral resting state of the eye (with the natural crystalline lens present) exists with the eye focused for objects in a range of about one meter to about two meters from the eye.

The starting point for accommodation in accordance with the present invention is at a neutral resting state of the eye, rather than infinity as in the previously discussed prior art accommodating IOLs which were biased in the posterior-most position with the eye at rest. In a neutral resting state of the mammalian or human eye, the parasympathetic/cholinergic system of the mammal or human maintains ciliary muscle tone, i.e., the ciliary muscle is partially contracted and zonular tension is partially relaxed. In this state, with a natural lens in place, the natural lens is spherical and in a forward position which increases the diffractive power of the eye. Thus, the eye, in the absence of visual stimuli, is in a neutral resting state or a "tonic accommodative" state and with appropriate stimulus is capable of both active or controlled positive accommodation and active or controlled negative accommodation. The present accommodating IOLs are able to adjust to distance (negative accommodation) and near (positive accommodation) in response to normal ciliary muscle action upon stimulation of the parasympathetic nervous system and/or the sympathetic nervous system.

In a very useful embodiment, the optic has a far (or distance) vision correction power for infinity (distance refraction) reduced by a diopter power increment in a range of more than 0.5 to about 2.5 or about 3.5 diopters, more preferably in a range of about 1 to about 2 diopters. Thus, the optic which is prescribed for the wearer of the IOL has a far vision correction power equal to the far vision correction power calculated or determined at infinity reduced by a diopter power increment, as described herein. This diopter power increment reduction often results in the IOL wearer experiencing relative myopia when viewing a distant object with the IOL in a neutral resting position in the eye. The present IOLs are adapted to move posteriorly in the eye from a resting position to provide negative accommodation, thereby alleviating this relative myopia.

The movement means or movement assembly acts, in cooperation with the eye, to move the optic both anteriorly and posteriorly to provide both positive and negative accommodation, respectively. In one embodiment, the movement means or movement assembly is coupled to the optic and is adapted to cooperate with the eye to move the optic anteriorly in the eye and posteriorly in the eye to effect positive accommodating movement of the optic and negative accommodating movement of the optic, respectively.

The present IOLs are preferably provided with a movement means or a movement assembly which, in cooperation with the eye, is adapted to provide an amount of positive accommodation in the range of about 1 to about 2.5 or about 3.5 diopters, and/or an amount of negative accommodation in the range of about 1 to about 2 or about 3 diopters. This range of both positive and negative accommodation is often effective to provide sufficient accommodation to patients suffering from presbyopia.

The present IOLs, and in particular the present optics, preferably are deformable, that is rollable, foldable or otherwise deformable, for insertion through a small incision, for example, on the order of no larger than about 4.0 mm or about 3.2 mm or about 2.8 mm in the eye.

The movement means or movement assembly may be adapted to be affixed to a capsular bag of the eye including the IOL.

In a particularly useful embodiment, the movement means or movement assembly circumscribes the optic. However, this is not an essential feature of the present invention and other structures and configurations can provide acceptable results. Having the movement means or movement assembly circumscribe the optic does allow the action of the ciliary muscle of the eye to have increased influence on the movement means or movement assembly since the ciliary muscle and zonules do circumscribe the capsular bag.

The movement means or movement assembly preferably comprises a movement member including a proximal end region coupled to, for example, integral or unitary with, the optic, and a distal end region extending away from the optic and adapted to contact the capsular bag of the eye. The movement means or movement assembly preferably is sufficiently flexible to facilitate movement of the optic, for example, anteriorly and posteriorly, in the eye relative to its distal end region upon being acted upon by the eye. In one useful embodiment, the movement means or assembly has a resiliency or springiness sufficient to enhance or amplify the movement of the optic in the eye upon being acted upon by the eye, thereby increasing the overall amount of accommodating movement attainable.

The movement means or movement assembly may include a hinge assembly positioned between the proximal end region and the distal end region of the movement member. Such hinge assembly is effective in facilitating the accommodating movement of the optic in the eye. The hinge assembly may include one or more regions of reduced thickness, for example, circumscribing the optic. In one embodiment, the movement means or movement assembly may include a plurality of spaced apart regions of reduced thickness. These reduced thickness regions are effective to provide a desired amount of flexibility to the movement means or movement assembly.

In a further broad aspect of the present invention, methods for inserting an IOL in an eye are provided. Such methods comprise providing an IOL in accordance with the present invention, as described herein. The IOL is placed into the eye, for example, in the capsular bag of the eye, using equipment and techniques which are conventional and well known in the art. The IOL is placed in a rest position in the eye, for example, a position so that the eye, and in particular the ciliary muscle and zonules of the eye, is approximately at a neutral or natural resting state, so that the eye effectively cooperates with the IOL to move the optic of the IOL anteriorly in the eye from the rest position to provide for positive focus accommodation, and posteriorly in the eye from the rest position to provide for negative focus accommodation. No treatments or medications, for example, to paralyze the ciliary muscle to facilitate fibrosis or otherwise influence the position of the IOL in the eye, are required. Preferably, the optic is deformed prior to being placed into the eye. Once the IOL is placed in the eye, and after a normal period of recovery from the surgical procedure, the IOL, in cooperation with the eye, provides the mammal or human wearing the IOL with both near focus accommodation and far (or distance) focus accommodation.

Any and all features described herein and combinations of such features are included within the scope of the present invention provided that the features of any such combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
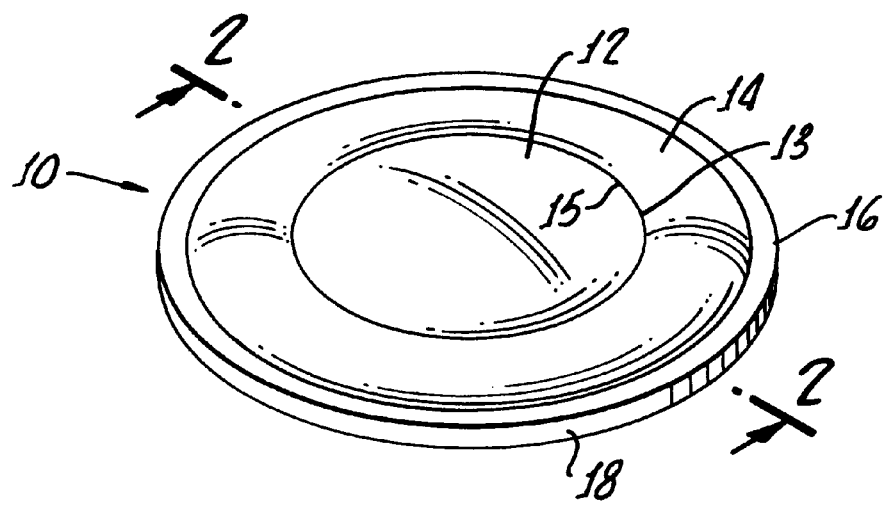
FIG. 1 is a top side view, in perspective, of an IOL in accordance with the present invention.
Figure 2:
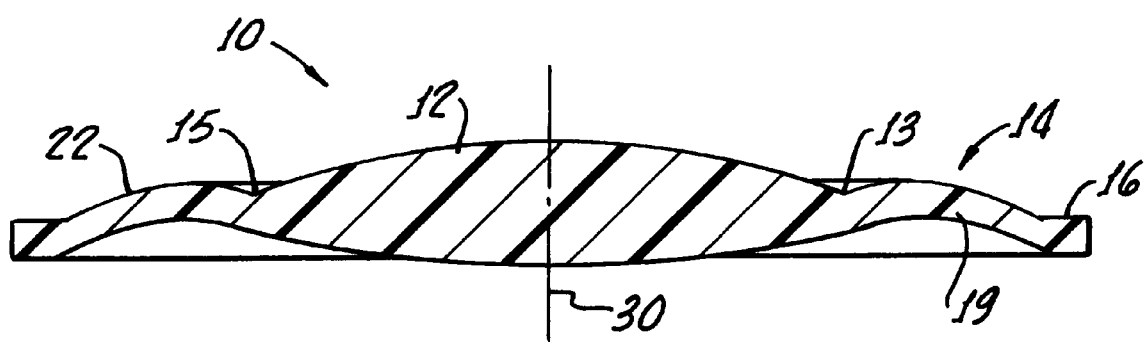
FIG. 2 is a cross sectional view taken generally along line 2—2 of FIG. 1.

Referring now to FIGS. 1 and 2, an IOL according to the present invention, shown generally at 10, includes a lens body or optic 12. Extending radially outwardly from lens body 12 is flexible member 14. Flexible member 14 circumscribes the optic 12, and has a proximal end portion 13 which is coupled to the optic at optic periphery 15. Flexible member 14 extends radially outwardly to a distal end region 16 including a peripheral surface 18. In between the proximal end region 13 and the distal end region 16, flexible member 14 includes an intermediate portion 19 which has a substantial degree of flexibility and springiness. Although it is not essential, flexible member 14 can be, and preferably is, integral or unitary with the optic 12. Flexible member 14 extends outwardly from optic 12 sufficiently so that the distal end region 16 is in contact with the inner peripheral wall of the posterior capsular bag when the IOL 10 is implanted in the eye.

The optic 12 may be constructed of rigid biocompatible materials, such as polymethyl methacrylate (PMMA), or flexible, deformable materials, such as silicone polymeric materials, acrylic polymeric materials, hydrogel polymeric materials and the like, which enable the optic 12 to be rolled or folded for insertion through a small incision into the eye. Although the optic 12 as shown is a refractive lens body, the present IOLs can include a diffractive lens body and such embodiment is included within the scope of the present invention.

Optic 12 is prescribed for the wearer of IOL 10 with a baseline or far (distance) diopter power for infinity reduced by 1.5 diopters. This baseline diopter power of optic 12 results in the wearer of IOL 10 experiencing relative myopia when viewing a far or distant object with the IOL at a neutral resting state or position of the eye. Such neutral resting state of the eye is approximately as shown in FIG. 3.

The flexible member 14, as shown, is integral (unitary) with and circumscribes the optic 12. Alternately, flexible member 14 can be mechanically or otherwise physically coupled to optic 12 and/or may not circumscribe the optic. For example, the flexible member may only partially circumscribe the optic, and such embodiment is included within the scope of the present invention. The flexible member 14 may be constructed of the same or different biocompatible materials as optic 12. The flexibility of flexible member 14 is sufficient to facilitate the bidirectional axial movement, that is bidirectional movement along the optical axis 30 (FIG. 2) of the optic 12 in the eye, as is described hereinafter. As shown in FIG. 2, flexible member 14 includes intermediate portion 19 which has sufficient springiness to be able to flex or vault between first and second positions, as is described hereinafter. The flexible member 14 preferably is deformable, in much the same manner as optic 12 is deformable, to facilitate passing IOL 10 through a small incision into the eye. The material or materials of construction from which flexible member is made are chosen to provide the flexible member with the desired degree of flexibility, springiness and/or deformability to meet the needs of the particular application involved.

The IOL 10 can be inserted into the capsular bag of a mammalian eye using conventional equipment and techniques, for example, after the natural crystalline lens of the eye is removed, using a phacoemulsification technique. The IOL 10 preferably is rolled or folded prior to insertion into the eye, and is inserted through a small incision, on the order of about 3.2 mm, into the eye and is located in the eye 40, as shown in FIG. 3.

Figure 3:
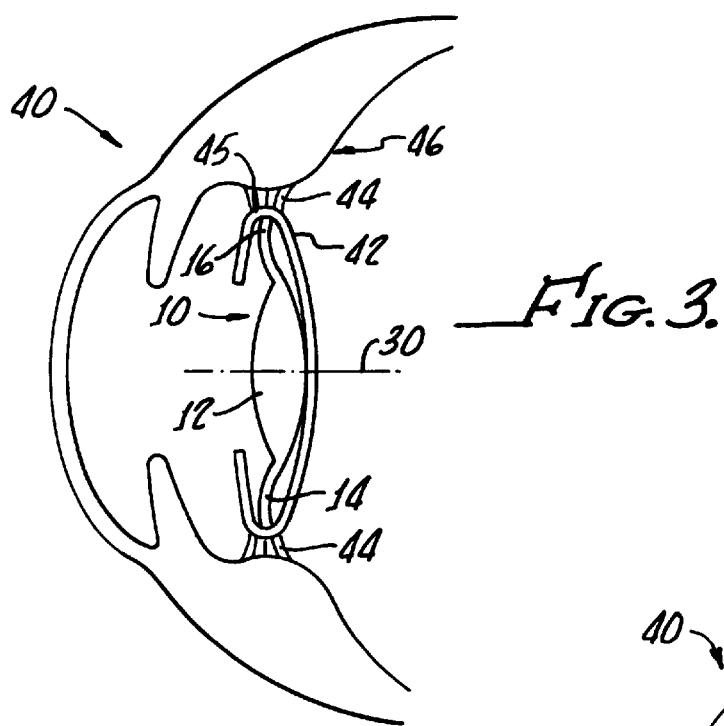
FIG. 3 is a fragmentary sectional view of an eye in which the IOL of FIG. 1 has been implanted, with the lens being located in a resting position with the eye approximately in a neutral resting state.

The IOL 10 in the eye 40, as shown in FIG. 3, is located in a resting position in the capsular bag 42 with the eye in approximately a neutral resting state. Although this initial positioning of IOL 10 in the eye 40 is preferred, it is important that the IOL be positioned so that the optic 12, in cooperation with the eye, can be moved both anteriorly and posteriorly in the eye from the resting position of the IOL to provide positive accommodation and negative accommodation, respectively. Over time, after the IOL 10 is implanted in eye 40, the resting position of the IOL may gradually adjust to a position at which the eye is approximately in a neutral resting state. The initial positioning of IOL 10 in eye 40 is not critical in the present invention. This is in direct contrast to the prior art accommodating IOLs noted previously in which the IOL is required to be located in the posterior-most position in the eye under rest or resting conditions.

The distal end region 16 of flexible member 14 is in contact with the interior wall 45 of the capsular bag 42. Over time, the distal end region 16 of the flexible member 14 may become affixed to the capsular bag 42, although this is not necessary to obtain benefits in accordance with the present invention. In the resting position, the flexible member 14 is in an unflexed condition or state, substantially as shown in FIG. 2.

The IOL 10 should be sized to facilitate the movement of the optic 12 in response to the action of ciliary muscle 46 and zonules 44. For example, if the optic 12 is too large, the ciliary muscle 46 and zonules 44 will be inhibited from effectively contracting/relaxing so that the amount of accommodating movement will be unduly restricted. Of course, if the IOL 10 is too small, the optic 12 will be ineffective to focus light on the retina of the eye 40, may cause glare and/or the flexible member 14 may not cooperate with the eye to effect the desired amount of accommodating movement. If the IOL 10 is to be included in an adult human eye, the optic 12 preferably has a diameter in the range of about 3.5 mm to about 7 mm, and the IOL has an overall maximum diameter, with the flexible member 14 in the unflexed state, in the range of about 8 mm to about 12 mm.

Figure 4:
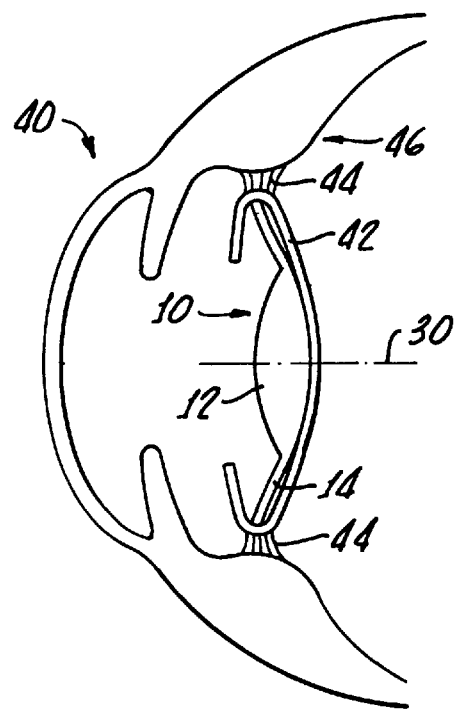
FIG. 4 is a fragmentary sectional view of an eye in which the IOL of FIG. 1 has been implanted, with the lens being located in a posterior position in the eye.

The zonules 44 of the ciliary muscle 46 are effective to move the capsular bag 42 and the IOL 10 included therein both anteriorly and posteriorly. Thus, further relaxation of the ciliary muscle 46 causes the zonules 44 to move the capsular bag 42 and the IOL 10 posteriorly into a posterior position, as shown in FIG. 4. This action of ciliary muscle 46 and zonules 44 causes flexible member 14 to flex or vault into a posterior position, as shown in FIG. 4, which enhances or increases (amplifies) the amount of posterior movement of optic 12. This posterior vaulting action of flexible member 14 increases the amount of negative (distance) accommodating movement of optic 12 relative to a similar IOL in which the flexible member does not include an intermediate portion, for example, such as intermediate portion 19, capable of flexing or vaulting. In effect, IOL 10 achieves increased accommodating axial movement because of such flexing or vaulting.

With IOL 10 in the posterior position, as shown in FIG. 4, far away or distant objects are brought into focus.

Figure 5:
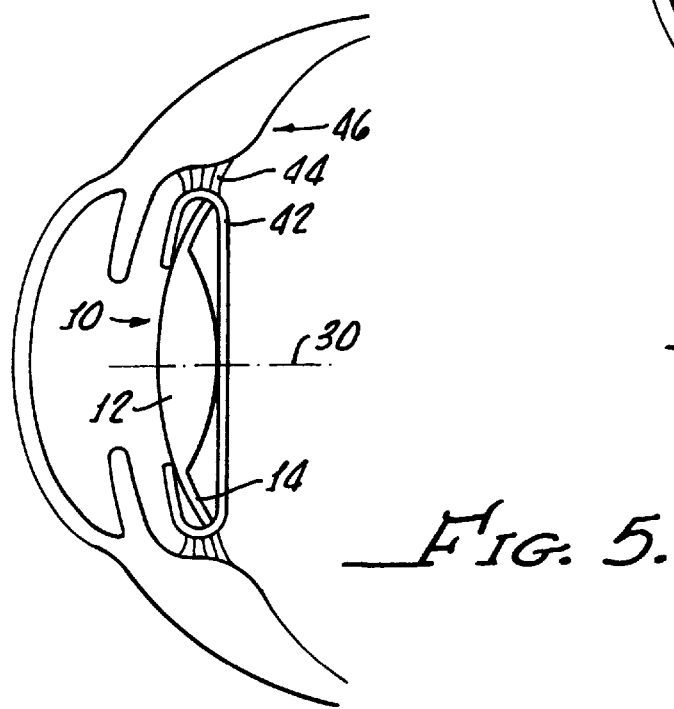
FIG. 5 is a fragmentary sectional view of an eye in which the IOL of FIG. 1 has been implanted, with the lens being located in an anterior position in the eye.

If a near object is to be viewed, the ciliary muscle 46 contracts or constricts causing the zonules 44 to move the capsular bag 42 and the IOL 10 included therein anteriorly relative to the rest position, as shown in FIG. 5. This action of ciliary muscle 46 and zonules 44 causes flexible member 14 to flex or vault into an anterior position, shown in FIG. 5, which enhances or increases (amplifies) the amount of anterior movement of optic 12. This anterior vaulting action of flexible member 14 increases the amount of positive (near) accommodating movement of optic 12 relative to a similar IOL in which the flexible member does not include an intermediate portion capable of flexing or vaulting. In effect, IOL 10 achieves increased accommodating movement because of such flexing or vaulting. This anterior movement of optic 12 provides near focus accommodation to allow the near object to be viewed.

The present IOL 10 has the ability, in cooperation with the eye, to move both posteriorly and anteriorly in the eye, to provide for both distance focus and near focus, respectively. This bidirectional movement of IOL 10 advantageously occurs in response to action of the ciliary muscle 46 and zonules 44 which action is substantially similar to that which effects accommodation in an eye having a natural crystalline lens. Thus, the ciliary muscle 46 and zonules 44 require little, if any, retraining to function in accordance with the present invention. The flexible member 14, as described herein, preferably is sufficiently flexible to facilitate or even enhance or accentuate the axial movement of the IOL 10 caused by the action of the ciliary muscle 46 and zonules 44 to provide increased positive and negative accommodation.

IOL 10 is such that the amount of positive or near accommodation preferably is in the range of about 1 to about 2.5 or about 3.5 diopters and the amount of negative or distance accommodation preferably is in the range of about 1 to about 2 diopters.

Figure 6:
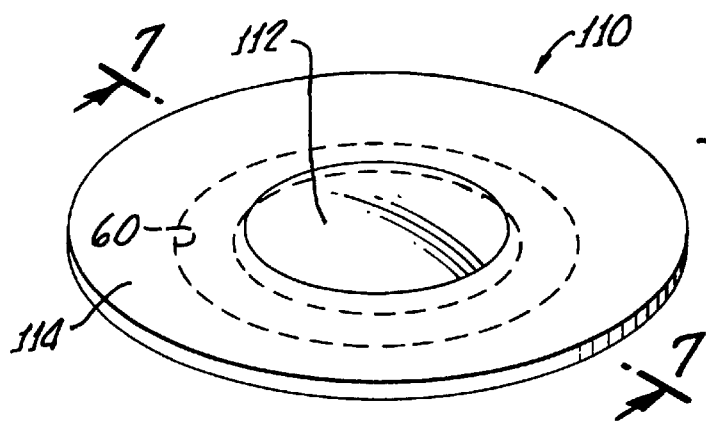
FIG. 6 is a top side view, in perspective, of an additional IOL in accordance with the present invention.
Figure 7:
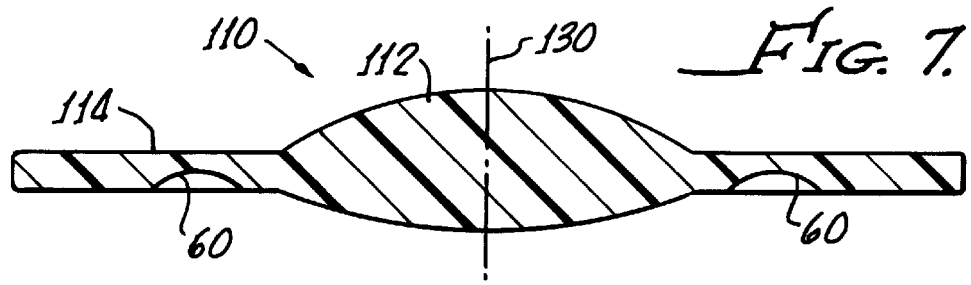
FIG. 7 is a cross sectional view taken generally along line 7—7 of FIG. 6.

FIGS. 6 and 7 illustrates an additional IOL, shown generally at 110, in accordance with the present invention. Except as expressly described herein, additional IOL 110 is structured and functions similarly to IOL 10. Components of IOL 110 which correspond to components of IOL 10 are indicated by the same reference numeral increased by 100.

The primary difference between IOL 110 and IOL 10 relates to the configuration of flexible member 114. In particular, as best shown in FIG. 7, flexible member 114 has a substantially flat general configuration, as opposed to the bowed (unflexed) configuration of flexible member 14.

Flexible member 114 includes a region 60 of reduced thickness which circumscribes the optic 112. Region 60, which has a generally rounded sidewall in cross-section (FIG. 7), in effect, operates to provide flexibility to flexible member 114. Such flexibility facilitates the axial movement of the optic 112 along axis 130 in the eye.

In the eye, IOL 110 moves bidirectionally in response to the action of the ciliary muscle 46 and zonules 44 in much the same manner as does IOL 10. The flexible member 114 does not have the ability to flex or vault as much as flexible member 14, as shown in FIGS. 4 and 5. Therefore, the range of accommodating movement of IOL 110 is somewhat less than the range of accommodating movement of IOL 10.

Figure 7A:
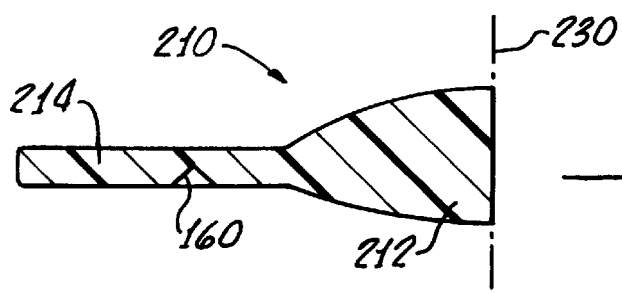
FIG. 7A is a partial cross sectional view of a similar IOL to that shown in FIG. 6 with an alternate hinge construction.

FIG. 7A is an illustration of an IOL 210, similar to IOL 110, in accordance with the present invention. Except as expressly described herein, IOL 210 is structured and functions similarly to IOL 110. Components of IOL 210 which correspond to components of IOL 110 are indicated by the same reference number increased by 100.

The primary difference between IOL 210 and IOL 110 relates to the configuration of the region 160 of reduced thickness which circumscribes the optic 212. Thus, flexible member 214 includes region 160 which has straight, mutually angled (intersecting) sidewalls in cross-section (FIG. 7A), as opposed to the rounded sidewall of region 60.

Region 160 operates to provide flexibility to flexible member 214. Such flexibility facilitates the axial movement of the optic 212 along axis 230 in the eye. In the eye, IOL 210 moves bidirectionally in response to the action of the ciliary muscle 46 and zonules 44 in much the same manner as does IOL 10.

The regions 60 and 160 can be considered hinges. Of course, other configurations, for example, other hinge configurations, which provide the desired degree of flexibility to the flexible members can be used and are included within the scope of the present invention.

Figure 8:
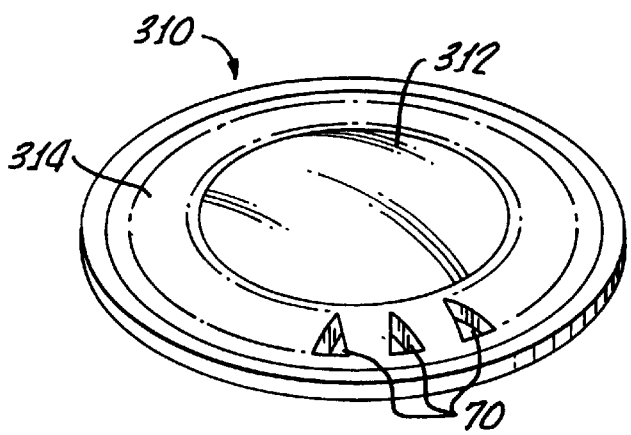
FIG. 8 is a top side view, in perspective, of a further IOL in accordance with the present invention.

FIG. 8 illustrates a further IOL, shown generally at 310, in accordance with the present invention. Except as expressly described herein, further IOL 310 is structured and functions similarly to IOL 10. Components of IOL 310 which correspond to components of IOL 10 are indicated by the same reference number increased by 300.

The primary difference between IOL 310 and IOL 10 relates to the construction of flexible member 314. In particular, flexible member 314 includes a series of sections 70 of reduced thickness which extend around the periphery 315 of optic 312. These sections 70 of reduced thickness provide desired flexibility to flexible member 314 to facilitate the posterior and anterior movement of optic 312 in the eye. In the eye, IOL 310 functions similarly to IOL 10 in providing both positive and negative focus accommodation.

The present invention provides bidirectional accommodating IOLs and methods for obtaining bidirectional accommodation using such IOLs. Bidirectional accommodation, as described herein, provides for both controlled positive accommodation and controlled negative accommodation. The overall extent of accommodation is often increased, for example, relative to previous accommodating IOLs.

While this invention has been described with respect to various specific examples and embodiments, it is to be understood that the invention is not limited thereto and that it can be variously practiced within the scope of the following claims.

What is claimed is:

1. An intraocular lens comprising:
    an optic adapted to focus light toward a retina of an eye, the optic having a far vision correction power for infinity reduced by a diopter power increment; and
    a movement assembly coupled to the optic and adapted to cooperate with the eye to move the optic anteriorly in the eye and posteriorly in the eye to effect positive accommodating movement of the optic and negative accommodating movement of the optic, respectively.

2. The intraocular lens of claim 1 wherein the optic has a far vision correction power for infinity reduced by a diopter power increment in a range of more than 0.5 to about 3.5 diopters.

3. The intraocular lens of claim 1 wherein the optic has a far vision correction power calculated for infinity and reduced by a diopter power increment in a range of about 1 to about 2 diopters.

4. The intraocular lens of claim 1 wherein the movement assembly, in cooperation with the eye, is adapted to provide an amount of positive accommodation in a range of about 1 to about 3.5 diopters, and an amount of negative accommodation in a range of about 1 to about 3 diopters.

5. The intraocular lens of claim 1 which is deformable for insertion through a small incision in the eye.

6. The intraocular lens of claim 1 wherein the optic has a diameter in the range of about 3.5 mm to about 7 mm and the intraocular lens has an overall diameter in the range of about 8 mm to about 12 mm.

7. The intraocular lens of claim 1 wherein the movement assembly is adapted to be affixed to a capsular bag of the eye including the intraocular lens.

8. The intraocular lens of claim 1 wherein the movement assembly circumscribes the optic, and comprises a member including a proximal end region coupled to the lens body and a distal end region extending away from the lens body and adapted to contact a capsular bag of the eye.

9. The intraocular lens of claim 8 wherein the movement assembly is sufficiently flexible to facilitate movement of the optic relative to its distal end region upon being acted upon by the eye.

10. The intraocular lens of claim 8 wherein the movement assembly includes a plurality of spaced apart portions of reduced thickness.

11. The intraocular lens of claim 8 wherein the movement assembly includes a hinge assembly positioned between the proximal end region and the distal end region.

12. The intraocular lens of claim 11 wherein the hinge assembly includes a region of reduced thickness circumscribing the optic.

13. An intraocular lens for the correction of presbyopia comprising:
    an optic adapted to focus light toward a retina of an eye;
    movement means adapted to act, in cooperation with the eye, to move the optic to provide an amount of positive accommodation in the range of about 1 to about 3.5 diopters, and an amount of negative accommodation in the range of about 1 to about 3 diopters.

14. The intraocular lens of claim 13 wherein the optic has a far vision correction power for infinity reduced by a diopter power increment in a range of more than 0.5 to about 3.5 diopters.

15. The intraocular lens of claim 13 wherein the optic has a far vision correction power which results in myopia at a neutral resting state of the eye.

16. The intraocular lens of claim 13 wherein the movement means comprises a member including a proximal end region coupled to the lens body and a distal end region extending away from the lens body and adapted to contact a capsular bag of the eye.

17. The intraocular lens of claim 13 wherein the member circumscribes the optic.

18. The intraocular lens of claim 13 wherein the optic has a diameter in the range of about 3.5 mm to about 7 mm and the intraocular lens has an overall diameter in the range of about 8 mm to about 12 mm.

19. A method of inserting an intraocular lens in an eye comprising:

providing an intraocular lens comprising an optic adapted to focus light toward a retina of an eye, the optic having a far vision correction power for infinity reduced by a diopter power increment and a movement assembly coupled to the optic and adapted to cooperate with the eye to move the optic anteriorly in the eye and posteriorly in the eye to effect positive accommodating movement of the optic and negative accommodating movement of the optic, respectively; and placing the intraocular lens into the eye in a rest position so that the eye effectively cooperates to move the optic anteriorly in the eye from the rest position and posteriorly in the eye from the rest position.

20. The method of claim 19 wherein the optic has a far vision correction power for infinity reduced by a diopter power increment in a range of more than 0.5 to about 3.5 diopters.

21. The intraocular lens of claim 19 wherein said placing step is effective to provide an amount of positive accommodation in a range of about 1 to about 3.5 diopters, and an amount of negative accommodation in a range of about 1 to about 3 diopters.

22. The method of claim 19 which further comprises deforming the optic prior to said placing step.

23. The method of claim 19 wherein the optic has a far vision correction power which results in myopia at a neutral resting state of the eye.

24. The method of claim 19 wherein the eye includes a ciliary muscle and zonules and the intraocular lens is sized to facilitate the movement of the optic in response to the action of the ciliary muscle and zonules.

25. The method of claim 24 wherein the optic has a diameter in the range of about 3.5 mm to about 7 mm and the intraocular lens has an overall diameter in the range of about 8 mm to about 12 mm.

* * * * *